US011547434B2

(12) United States Patent
McGuckin, Jr. et al.

(10) Patent No.: US 11,547,434 B2
(45) Date of Patent: *Jan. 10, 2023

(54) ATHERECTOMY DEVICE

(71) Applicant: Rex Medical, L.P., Conshohocken, PA (US)

(72) Inventors: James F. McGuckin, Jr., Radnor, PA (US); John D. Leedle, Philadelphia, PA (US); Colin Valentis, Lansdale, PA (US); Jenna Rose Israel, Philadelphia, PA (US)

(73) Assignee: REX MEDICAL L.P., Conshohocken, PA (US)

( * ) Notice: Subject to any disclaimer, the term of this patent is extended or adjusted under 35 U.S.C. 154(b) by 451 days.

This patent is subject to a terminal disclaimer.

(21) Appl. No.: 16/593,497

(22) Filed: Oct. 4, 2019

(65) Prior Publication Data

US 2020/0029999 A1    Jan. 30, 2020

Related U.S. Application Data

(63) Continuation of application No. 14/948,172, filed on Nov. 20, 2015, now Pat. No. 10,463,389.

(Continued)

(51) Int. Cl.
*A61B 17/3207* (2006.01)
*A61B 17/00* (2006.01)
(Continued)

(52) U.S. Cl.
CPC ............ *A61B 17/320758* (2013.01); *A61B 2017/00685* (2013.01); *A61B 2017/22038* (2013.01);
(Continued)

(58) Field of Classification Search
CPC ............ A61B 17/3207–2017/320791; A61B 17/32002–2017/320032; A61B 2017/00685; A61F 9/00763
See application file for complete search history.

(56) References Cited

U.S. PATENT DOCUMENTS 4,445,509 A * 5/1984 Auth ................ A61B 17/22031
606/159
4,883,458 A    11/1989 Shiber
(Continued)

FOREIGN PATENT DOCUMENTS

CN    102670283    9/2012
EP    2 913 012    9/2015
(Continued)

OTHER PUBLICATIONS

The Extended European Search Report Application No. 15200337.2 dated Nov. 18, 2020.
(Continued)

*Primary Examiner* — Tan-Uyen T Ho
*Assistant Examiner* — Charles M Wei
(74) *Attorney, Agent, or Firm* — Neil D. Gershon

(57) ABSTRACT

An atherectomy device for removing deposits such as plaque from an interior of a vessel including an outer member and a rotatable shaft positioned for rotational movement within the outer member and fixed axially within the outer member. A tip is mounted to the distal region of the rotatable shaft and is positioned distally of the distal end of the outer member to create a gap between the proximal end of the rotatable tip and the distalmost edge of the outer member. The rotatable tip has a longitudinal axis mounted to the rotatable shaft for rotation about its longitudinal axis upon rotation of the shaft, the shaft including a guidewire lumen for receiving a guidewire to enable over the wire insertion of the device.

16 Claims, 10 Drawing Sheets

Related U.S. Application Data

(60) Provisional application No. 62/097,049, filed on Dec. 27, 2014.

(51) Int. Cl.
  *A61B 17/22* (2006.01)
  *A61B 17/32* (2006.01)

(52) U.S. Cl.
  CPC ............ *A61B 2017/22079* (2013.01); *A61B 2017/22094* (2013.01); *A61B 2017/320004* (2013.01); *A61B 2017/320716* (2013.01); *A61B 2017/320775* (2013.01)

(56) References Cited

U.S. PATENT DOCUMENTS

| | | | |
|---|---|---|---|
| 4,957,482 A * | 9/1990 | Shiber | A61B 17/320783 604/22 |
| 4,979,939 A | 12/1990 | Shiber | |
| 4,990,134 A * | 2/1991 | Auth | A61B 17/22031 604/22 |
| 5,019,089 A * | 5/1991 | Farr | A61B 17/320758 606/159 |
| 5,047,040 A * | 9/1991 | Simpson | A61B 17/320758 606/159 |
| 5,114,399 A | 5/1992 | Kovalcheck | |
| 5,217,474 A | 6/1993 | Zacca et al. | |
| 5,273,526 A * | 12/1993 | Dance | A61B 17/22 604/35 |
| 5,287,858 A * | 2/1994 | Hammerslag | A61B 17/320758 600/585 |
| 5,306,244 A | 4/1994 | Shiber | |
| 5,308,354 A | 5/1994 | Zacca et al. | |
| 5,312,427 A * | 5/1994 | Shturman | A61B 17/3207 606/159 |
| 5,314,438 A * | 5/1994 | Shturman | A61B 17/320758 606/159 |
| 5,356,418 A | 10/1994 | Shturman | |
| 5,490,859 A * | 2/1996 | Mische | A61B 17/320725 606/159 |
| 5,584,843 A * | 12/1996 | Wulfman | A61B 17/320758 604/22 |
| 5,632,755 A | 5/1997 | Nordgren et al. | |
| 5,653,696 A * | 8/1997 | Shiber | A61B 17/3207 604/267 |
| 5,667,490 A * | 9/1997 | Keith | A61B 17/3207 173/220 |
| 5,681,336 A * | 10/1997 | Clement | A61B 17/320758 604/96.01 |
| 5,728,129 A | 3/1998 | Summers | |
| 5,779,721 A | 7/1998 | Nash | |
| 5,794,626 A * | 8/1998 | Kieturakis | A61B 10/0266 600/567 |
| 5,873,882 A | 2/1999 | Straub et al. | |
| 5,876,414 A * | 3/1999 | Straub | A61B 17/320783 606/159 |
| 5,879,361 A | 3/1999 | Nash | |
| 5,938,670 A | 8/1999 | Keith et al. | |
| 5,938,672 A | 8/1999 | Nash | |
| 5,951,581 A | 9/1999 | Saadat | |
| 5,976,165 A | 11/1999 | Ball et al. | |
| 6,001,112 A | 12/1999 | Taylor | |
| 6,015,420 A * | 1/2000 | Wulfman | A61B 17/320758 604/22 |
| 6,066,152 A | 5/2000 | Strauss et al. | |
| 6,077,282 A | 6/2000 | Shturman et al. | |
| 6,080,170 A | 6/2000 | Nash et al. | |
| 6,090,118 A | 7/2000 | McGuckin, Jr. | |
| 6,113,615 A | 9/2000 | Wulfman | |
| 6,132,444 A * | 10/2000 | Shturman | A61B 17/320758 128/858 |
| 6,146,395 A | 11/2000 | Kanz et al. | |
| 6,156,046 A | 12/2000 | Passafaro et al. | |
| 6,156,048 A | 12/2000 | Wulfman | |
| 6,183,487 B1 * | 2/2001 | Barry | A61B 17/320758 606/159 |
| 6,206,898 B1 | 3/2001 | Honeycutt et al. | |
| 6,270,509 B1 | 8/2001 | Barry et al. | |
| 6,299,623 B1 | 10/2001 | Wulfman | |
| 6,443,967 B1 | 9/2002 | Kadavy et al. | |
| 6,454,779 B1 | 9/2002 | Taylor | |
| 6,482,216 B1 | 11/2002 | Hiblar et al. | |
| 6,491,660 B2 | 12/2002 | Guo et al. | |
| 6,494,890 B1 | 12/2002 | Shturman et al. | |
| 6,497,711 B1 | 12/2002 | Plaia et al. | |
| 6,565,588 B1 * | 5/2003 | Clement | A61B 17/320725 604/22 |
| 6,569,147 B1 | 5/2003 | Evans et al. | |
| 6,569,177 B1 | 5/2003 | Dillard et al. | |
| 6,572,630 B1 * | 6/2003 | McGuckin, Jr. | A61B 17/320758 606/159 |
| 6,579,298 B1 | 6/2003 | Bruneau et al. | |
| 6,579,299 B2 * | 6/2003 | McGuckin, Jr. | A61B 17/320758 606/159 |
| 6,596,005 B1 | 7/2003 | Kanz et al. | |
| 6,602,264 B1 | 8/2003 | McGuckin, Jr. | |
| 6,626,890 B2 | 9/2003 | Nguyen et al. | |
| 6,632,230 B2 | 10/2003 | Barry | |
| 6,652,546 B1 | 11/2003 | Nash et al. | |
| 6,702,830 B1 | 3/2004 | Demarais et al. | |
| 6,752,630 B2 | 6/2004 | Roetzer | |
| 6,808,531 B2 | 10/2004 | Lafontaine et al. | |
| 6,824,550 B1 | 11/2004 | Noriega et al. | |
| 6,830,577 B2 | 12/2004 | Nash et al. | |
| 6,843,797 B2 | 1/2005 | Nash et al. | |
| 6,905,505 B2 | 6/2005 | Nash et al. | |
| 6,926,725 B2 | 8/2005 | Cooke et al. | |
| 6,936,056 B2 | 8/2005 | Nash et al. | |
| 7,037,316 B2 | 5/2006 | McGuckin, Jr. et al. | |
| 7,172,610 B2 | 2/2007 | Heitzmann et al. | |
| 7,479,147 B2 | 1/2009 | Honeycutt et al. | |
| 7,534,249 B2 | 5/2009 | Nash et al. | |
| 7,645,261 B2 | 1/2010 | Hinchliffe | |
| 7,655,016 B2 * | 2/2010 | Demarais | A61B 17/320725 606/159 |
| 7,666,161 B2 | 2/2010 | Nash et al. | |
| 7,713,231 B2 | 5/2010 | Wulfman et al. | |
| 7,771,445 B2 | 8/2010 | Heitzmann et al. | |
| 7,833,239 B2 | 11/2010 | Nash | |
| 7,905,896 B2 | 3/2011 | Straub | |
| 7,959,608 B2 | 6/2011 | Nash et al. | |
| 7,976,528 B2 | 7/2011 | Nash et al. | |
| 7,981,128 B2 | 7/2011 | To et al. | |
| 7,981,129 B2 | 7/2011 | Nash et al. | |
| 8,007,506 B2 | 8/2011 | To et al. | |
| 8,062,317 B2 | 11/2011 | McGuckin, Jr. et al. | |
| 8,109,954 B2 * | 2/2012 | Shturman | A61B 17/3207 606/159 |
| 8,142,458 B2 | 3/2012 | Shturman | |
| 8,226,673 B2 | 7/2012 | Nash et al. | |
| 8,236,016 B2 | 8/2012 | To et al. | |
| 8,323,240 B2 | 12/2012 | Wulfman et al. | |
| 8,348,965 B2 | 1/2013 | Prudnikov et al. | |
| 8,353,922 B2 | 1/2013 | Noriega | |
| 8,353,923 B2 * | 1/2013 | Shturman | F16L 55/26 606/159 |
| 8,361,094 B2 | 1/2013 | To et al. | |
| 8,361,097 B2 | 1/2013 | Patel et al. | |
| 8,388,582 B2 | 3/2013 | Eubanks et al. | |
| 8,414,543 B2 | 4/2013 | McGuckin, Jr. et al. | |
| 8,439,937 B2 | 5/2013 | Montague et al. | |
| 8,465,511 B2 | 6/2013 | McGuckin, Jr. et al. | |
| 8,475,484 B2 | 7/2013 | Wulfman et al. | |
| 8,551,128 B2 | 10/2013 | Hanson et al. | |
| 8,568,432 B2 | 10/2013 | Straub | |
| 8,574,249 B2 | 11/2013 | Moberg | |
| 8,579,851 B2 | 11/2013 | Cull | |
| 8,597,313 B2 | 12/2013 | Thatcher et al. | |

(56) References Cited

U.S. PATENT DOCUMENTS

| | | | |
|---|---|---|---|
| 8,628,549 B2* | 1/2014 | To | A61B 17/320758 606/159 |
| 8,628,550 B2 | 1/2014 | Narveson et al. | |
| 8,628,551 B2 | 1/2014 | Hanson et al. | |
| 8,632,557 B2 | 1/2014 | Thatcher et al. | |
| 8,663,259 B2 | 3/2014 | Levine et al. | |
| 8,663,261 B2 | 3/2014 | Shturman | |
| 8,702,735 B2 | 4/2014 | Rivers | |
| 8,758,377 B2 | 6/2014 | Rivers et al. | |
| 8,764,779 B2 | 7/2014 | Levine et al. | |
| 8,795,303 B2 | 8/2014 | McBroom et al. | |
| 8,795,304 B2 | 8/2014 | Svendsen et al. | |
| 8,795,306 B2 | 8/2014 | Smith et al. | |
| 8,882,680 B2 | 11/2014 | Furlong et al. | |
| 8,888,801 B2 | 11/2014 | To et al. | |
| 8,920,402 B2 | 12/2014 | Nash et al. | |
| 9,023,070 B2 | 5/2015 | Levine et al. | |
| 9,028,424 B2 | 5/2015 | Furlong et al. | |
| 9,033,864 B2 | 5/2015 | Furlong et al. | |
| 9,033,895 B2 | 5/2015 | Furlong et al. | |
| 9,050,126 B2 | 6/2015 | Rivers et al. | |
| 9,055,966 B2 | 6/2015 | Cambronne et al. | |
| 9,072,505 B2 | 7/2015 | Furlong et al. | |
| 9,113,945 B2 | 8/2015 | Malla et al. | |
| 9,119,660 B2 | 9/2015 | Rivers et al. | |
| 9,119,661 B2 | 9/2015 | Rivers et al. | |
| 9,211,138 B2 | 12/2015 | Shturman | |
| 9,320,535 B2* | 4/2016 | Zaretzka | A61B 17/320725 |
| 9,675,376 B2 | 6/2017 | To | |
| 2001/0037121 A1 | 5/2001 | Suhy et al. | |
| 2002/0007190 A1* | 1/2002 | Wulfman | A61B 17/320758 606/167 |
| 2002/0099367 A1 | 7/2002 | Guo et al. | |
| 2002/0138088 A1 | 9/2002 | Nash | |
| 2003/0125757 A1* | 7/2003 | Patel | A61B 17/320783 606/159 |
| 2003/0199889 A1 | 10/2003 | Kanz et al. | |
| 2004/0219028 A1 | 11/2004 | Demarais et al. | |
| 2004/0243162 A1 | 12/2004 | Wulfman et al. | |
| 2005/0080478 A1* | 4/2005 | Barongan | A61B 17/320725 623/1.14 |
| 2005/0119678 A1* | 6/2005 | O'Brien | A61B 17/320758 606/159 |
| 2005/0149084 A1 | 7/2005 | Kanz et al. | |
| 2007/0162062 A1 | 7/2007 | Norton | |
| 2008/0004643 A1 | 1/2008 | To et al. | |
| 2009/0018565 A1* | 1/2009 | To | A61B 17/320758 606/159 |
| 2009/0024085 A1 | 1/2009 | To et al. | |
| 2011/0040315 A1 | 2/2011 | To et al. | |
| 2011/0106051 A1 | 5/2011 | Saab | |
| 2011/0270289 A1 | 11/2011 | To et al. | |
| 2012/0071907 A1 | 3/2012 | Pintor et al. | |
| 2012/0130410 A1 | 5/2012 | Tal et al. | |
| 2012/0211542 A1 | 8/2012 | Racenet | |
| 2013/0018398 A1 | 1/2013 | Rivers et al. | |
| 2013/0018399 A1 | 1/2013 | Rivers et al. | |
| 2013/0023913 A1 | 1/2013 | Rivers et al. | |
| 2013/0103046 A1 | 4/2013 | Shiber | |
| 2013/0178868 A1 | 7/2013 | Roh | |
| 2013/0245704 A1 | 9/2013 | Koltz et al. | |
| 2013/0253552 A1 | 9/2013 | Schoenle et al. | |
| 2014/0148830 A1* | 5/2014 | Bowman | A61B 17/320758 606/159 |
| 2014/0200599 A1 | 7/2014 | Shiber | |
| 2014/0316451 A1 | 10/2014 | Higgins et al. | |
| 2014/0330286 A1 | 11/2014 | Wallace | |
| 2015/0051626 A1 | 2/2015 | Rivers et al. | |
| 2015/0094748 A1 | 4/2015 | Nash et al. | |
| 2015/0164542 A1 | 6/2015 | Wulfman et al. | |
| 2015/0245851 A1 | 9/2015 | McGuckin, Jr. | |
| 2015/0342682 A1 | 12/2015 | Bowe | |

FOREIGN PATENT DOCUMENTS

| | | |
|---|---|---|
| NL | 1034242 | 8/2008 |
| WO | WO 1994/10919 | 5/1994 |
| WO | WO 1998/004199 | 2/1998 |
| WO | WO 2001/19444 | 3/2001 |
| WO | WO 2001/076680 | 10/2001 |
| WO | WO 2002/26289 | 4/2002 |
| WO | WO 2008/097993 | 8/2008 |
| WO | WO 2008/155759 | 12/2008 |
| WO | WO 2012/088167 | 6/2012 |
| WO | WO 2014/91881 | 6/2014 |
| WO | WO 2014/163942 | 10/2014 |

OTHER PUBLICATIONS

The Extended European Search Report Application No. 15155876.4 dated Jul. 6, 2015.

The Extended European Search Report Application No. 15200337.2 dated Apr. 28, 2016.

European Search Report for application 17161776.4-1659 dated Jul. 2017.

The Extended European Search Report Application No. 16187574.5 dated Jan. 30, 2017.

* cited by examiner

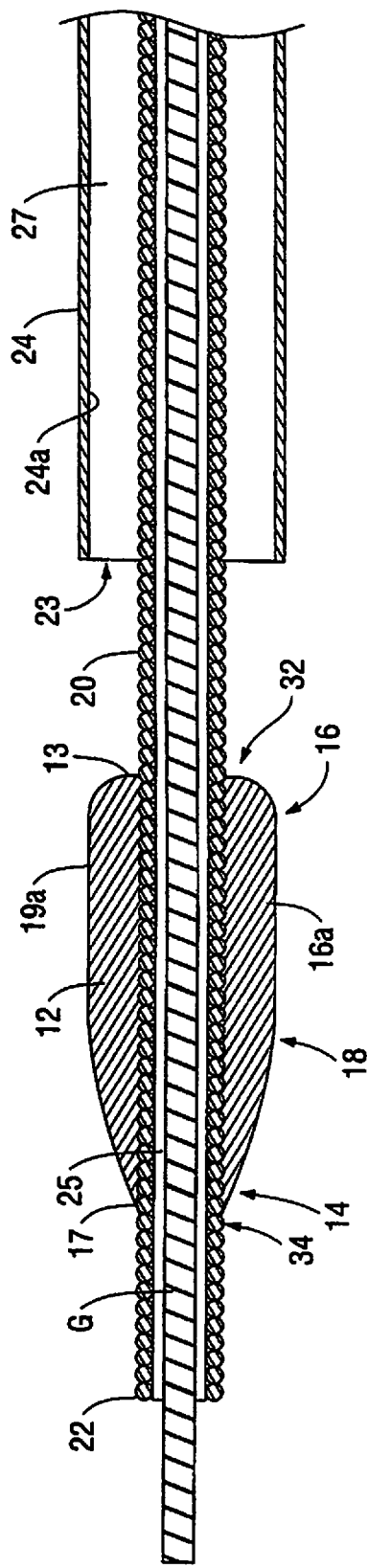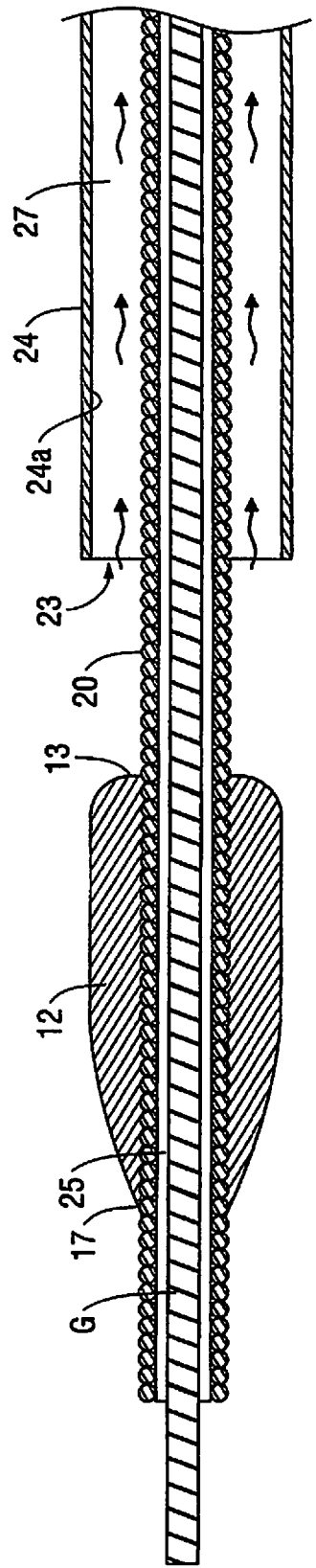

ATHERECTOMY DEVICE

BACKGROUND

This application is a continuation of U.S. application Ser. No. 14/948,172, filed on Nov. 20, 2015, which claims priority from provisional application, 62/097,049, filed Dec. 27, 2014. The entire contents of each of these applications are incorporated herein by reference.

TECHNICAL FIELD

This application relates to a vascular surgical apparatus, and more particularly to a minimally invasive device for removing plaque or other deposits from the interior of a vessel.

BACKGROUND OF RELATED ART

The vascular disease of atherosclerosis is the buildup of plaque or substances inside the vessel wall which reduces the size of the passageway through the vessel, thereby restricting blood flow. Such constriction or narrowing of the passage in the vessel is referred to as stenosis. In the case of peripheral vascular disease, which is atherosclerosis of the vascular extremities, if the vessel constriction is left untreated, the resulting insufficient blood flow can cause claudication and possibly require amputation of the patient's limb. In the case of coronary artery disease, if left untreated, the blood flow through the coronary artery to the myocardium will become inadequate causing myocardial infarction and possibly leading to stroke and even death.

There are currently several different treatments for treating arterial disease. The most invasive treatment is major surgery. With peripheral vascular diseases, such as occlusion of the tibial artery, major surgery involves implantation and attachment of a bypass graft to the artery so the blood flow will bypass the occlusion. The surgery involves a large incision, e.g., a 10 inch incision in the leg, is expensive and time consuming for the surgeon, increases patient pain and discomfort, results in a long patient recovery time, and has the increased risk of infection with the synthetic graft.

Major surgery for treating coronary artery disease is even more complex. In this surgery, commonly referred to as open heart surgery, a bypass graft connects the heart to the vessel downstream of the occlusion, thereby bypassing the blockage. Bypass surgery requires opening the patient's chest, is complex, has inherent risks to the patient, is expensive and requires lengthy patient recovery time. Bypass surgery also requires use of a heart lung machine to pump the blood as the heart is stopped, which has its own risks and disadvantages. Oftentimes, the saphenous vein in the patient's leg must be utilized as a bypass graft, requiring the additional invasive leg incision which further complicates the procedure, increases surgery time, lengthens the patient's recovery time, can be painful to the patient, and increases the risk of infection.

Attempts to minimize the invasiveness of coronary bypass surgery are currently being utilized in certain instances. These typically include creating a "window approach" to the heart. Although the window approach may reduce patient trauma and recovery time relative to open heart surgery, it still requires major surgery, and is a complicated and difficult surgery to perform due to limited access and limited instrumentation for successfully performing the operation. Attempts to avoid the use of a heart lung machine by using heart stabilization methods has become more accepted, but again, this does not avoid major surgery.

Due to the invasiveness and potential for complications with major peripheral or coronary vascular surgery, minimally invasive procedures have been developed. Balloon angioplasty is one of the minimally invasive methods for treating vessel occlusion and obstructions. A catheter having a balloon is inserted through the access artery, e.g., the femoral artery in the patient's leg or the radial artery in the arm, and advanced through the vascular system to the occluded site over a guidewire. The deflated balloon is placed at the occlusion and inflated to crack and stretch the plaque and other deposits to expand the opening in the vessel. Balloon angioplasty, especially in coronary surgery, is frequently immediately followed by insertion of a stent, a small metallic expandable device which is placed inside the vessel wall to retain the opening which was created by the balloon. Balloon angioplasty has several drawbacks including difficulty in forcing the balloon through the partially occluded passageway if there is hard occlusion, the risk involved in cutting off blood flow when the balloon is fully inflated, the frequency of restenosis after a short period of time since the plaque is essentially stretched or cracked and not removed from the vessel wall or because of the development of intimal hyperplasia and the possibility of balloon rupture when used in calcified lesions.

Another minimally invasive technique used to treat arteriosclerosis is referred to as atherectomy and involves removal of the plaque by a cutting or abrading instrument. This technique provides a minimally invasive alternative to the bypass surgery techniques described above and can provide an advantage over balloon angioplasty methods in certain instances. Atherectomy procedures typically involve inserting a cutting or ablating device through the access artery, e.g., the femoral artery or the radial artery, and advancing it over a guidewire through the vascular system to the occluded region, and rotating the device at high speed to cut through or ablate the plaque. The removed plaque or material can then be suctioned out of the vessel or be of such fine diameter that it is cleared by the reticuloendothelial system. Removal of the plaque in an atherectomy procedure has an advantage over balloon angioplasty plaque displacement since it debulks the material.

Examples of atherectomy devices in the prior art include U.S. Pat. Nos. 4,990,134, 5,681,336, 5,938,670, and 6,015,420. These devices have elliptical shaped tips which are rotated at high speeds to cut away the plaque and other deposits on the interior vessel wall. A well-known device is marketed by Boston Scientific Corp. and referred to as the Rotablator. As can be appreciated, in these devices, the region of plaque removal is dictated by the outer diameter of the cutting tip (burr) since only portions of the plaque contacted by the rotating tip are removed. The greater the area of plaque removed, the larger passageway created through the vessel and the better the resulting blood flow.

U.S. Pat. Nos. 5,217,474 and 6,096,054 disclose expandable cutting tips. These tips however are quite complex and require additional expansion and contraction steps by the surgeon.

U.S. Pat. No. 6,676,698 discloses an atherectomy device designed to obtain an optimal balance between the competing objectives of the smallest introducer sheath size to facilitate insertion and reduce trauma to the vessel and the largest atherectomy tip size to remove a larger region of plaque or other deposits from the vessel wall.

However it would be advantageous to enhance the breaking up and removal of the small particles in atherectomy procedures.

SUMMARY

The present invention provides in one aspect an atherectomy device for removing deposits such as plaque from an interior of a vessel comprising an outer member having a distal end, a rotatable shaft positioned for rotational movement within the outer member and fixed axially within the outer member and having a longitudinal axis, a distal region and a distalmost edge, and a rotatable tip having a proximal end and a distal end. The proximal end of the rotatable tip is positioned distally of the distal end of the outer member to create a gap between the proximal end of the rotatable tip and the distalmost edge of the outer member. The rotatable tip is mounted to the distal region of the rotatable shaft. The rotatable tip has a longitudinal axis and is mounted to the rotatable shaft for rotation about its longitudinal axis upon rotation of the shaft, the shaft including a guidewire lumen for receiving a guidewire to enable over the wire insertion of the device.

In some embodiments, the device includes an auger positioned on the rotatable shaft, the auger positioned proximally of the rotatable tip and distally of a distalmost edge of the outer member, wherein rotation of the shaft rotates the auger to move particles abraded by the tip proximally into the outer member.

In some embodiments, particles are aspirated through the outer member in the space between the rotatable shaft and an inner wall of the outer member.

In some embodiments, the rotatable tip has a scalloped region at an intermediate region. In some embodiments, the rotatable tip is made of first and second materials, the first material having a first density and the second material having a second density less than the first density. In some embodiments, the material of a first density is on one side of the tip and the material of the second density is on the other side of the tip. Examples of materials include tungsten carbide and aluminum. In some embodiments, the rotatable tip has a first region on one side of a longitudinal axis of the shaft and a second region on an opposing side of the longitudinal axis of the shaft, and the first region has a cutout so a first amount of material in the first region is less than a second amount of material in the second region.

In some embodiments, the rotatable tip can be mounted proximal of the distalmost edge of the rotatable shaft.

The tip can have a lumen extending therethrough dimensioned to receive the rotatable shaft.

In some embodiments, the rotatable tip is composed of first and second components, e.g., halves, the components radially spaced from each other. In some embodiments, the first component is composed of a material having a density greater than a density of the second component. In some embodiments, the first component has a portion removed so it is composed of less material than the second component.

In accordance with another aspect of the present disclosure, an atherectomy device for removing deposits such as plaque from an interior of a vessel is provided comprising an outer member having a distal end, a rotatable shaft positioned for rotational movement within the outer member and fixed axially within the outer member and having a longitudinal axis, a distal region and a distalmost edge. A rotatable tip has a proximal end and a distal end, the proximal end positioned distally of the distalmost edge of the outer member to create a gap between the proximal end of the rotatable tip and the distalmost edge of the outer member. The rotatable tip is mounted to the distal region of the rotatable shaft and has a longitudinal axis and is mounted to the rotatable shaft for rotation about its longitudinal axis upon rotation of the rotatable shaft. The rotatable shaft includes a guidewire lumen for receiving a guidewire to enable over the wire insertion of the device. The rotating tip has a first portion and a second portion, the first portion being different than the second portion.

In some embodiments, the device further includes an auger positioned on the rotatable shaft, the auger positioned proximally of the rotatable tip and extending along the rotatable shaft, wherein rotation of the rotatable shaft rotates the auger to move particles macerated by the rotatable tip proximally into the outer member.

In accordance with another aspect of the present disclosure a method for removing deposits such as plaque from an interior of a vessel is provided. The method comprises the steps of:

providing an introducer sheath having an internal diameter;

providing a deposit removal device including an outer member, a rotatable shaft and a rotating tip at a distal portion of the shaft, the rotating tip having a first portion and a second portion, the first portion being different than the second portion, the tip having a transverse cross-sectional dimension;

inserting the introducer sheath through a skin incision and into a vessel, advancing the tip adjacent the deposits to be removed; and actuating a motor to rotate the tip at high speed to contact and remove the deposits, the tip rotating to remove deposits in a cross-sectional area greater than the transverse cross-sectional dimension of the tip.

The method can in some embodiments further include the step of aspirating deposits through a space in the outer member between the shaft and an inner wall of the outer member. The rotatable shaft can have a screw thread so the step of rotating the shaft causes the external screw thread of the shaft to direct particles proximally.

The method in some embodiments further includes the step of applying a vacuum to aspirate proximally deposits removed by rotational movement of the tip.

In some embodiments, the device includes an outer member and the shaft is rotatably positioned within the outer member and particles are aspirated in a gap between an outer diameter of the shaft and an inner diameter of the outer member.

The method can further include the step of inserting the tip and shaft over a guidewire.

In some embodiments, the first and second portions differ by the first portion having a cutout to remove material from the first portion. In some embodiments, the first and second portions differ by the first portion having a first density and the second portion having a second density less than the first density.

BRIEF DESCRIPTION OF THE DRAWINGS

Preferred embodiment(s) of the present disclosure are described herein with reference to the drawings wherein:

FIG. 2 is a cross-sectional view of the distal portion of the atherectomy device of FIG. 1;

FIG. 3 is a view similar to FIG. 2 showing aspiration through the catheter;

FIGS. 12A-12D show a method of use of the atherectomy device of FIG. 4 wherein:

FIG. 12A is a side view in partial cross-section of the guidewire being inserted through the vessel;

FIG. 12B is a side view in partial cross-section illustrating the rotating shaft and bit of the atherectomy device inserted over the guidewire;

FIG. 12C is a view similar to FIG. 12B showing rotation of the shaft to remove plaque;

FIG. 12D is a view similar to FIG. 12C showing further removal of the plaque.

DETAILED DESCRIPTION OF PREFERRED EMBODIMENTS

Figure 1:
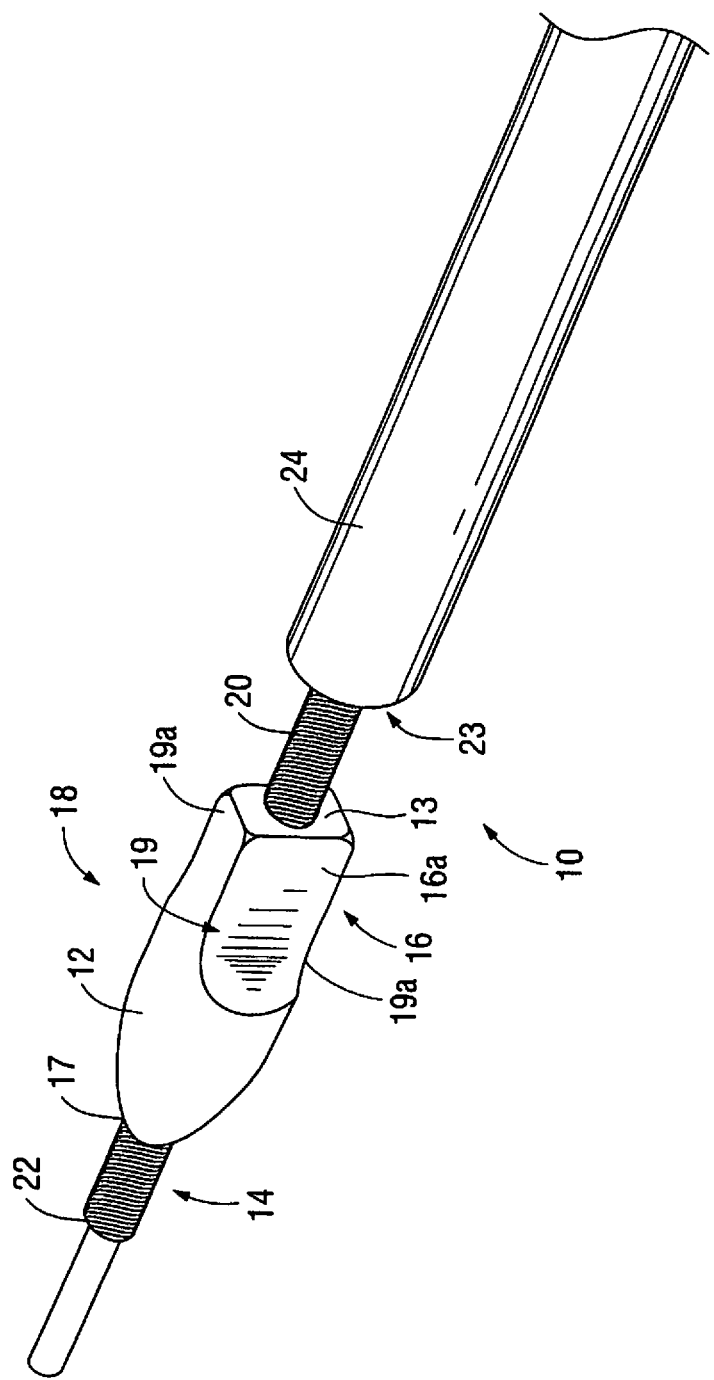
FIG. 1 is a perspective view of the distal portion of the atherectomy device of one embodiment of the present invention.

The present invention is directed to an atherectomy device designed for high speed rotation to remove plaque or other deposits on the inside wall of the vessel to widen the blood passageway therethrough. To achieve such rotation, the atherectomy tip is positioned at a distal end of a flexible rotating shaft that can be gas or electrically powered. The shaft rotates at high speed, typically between 100,000 and 200,000 rpm, causing the cutting or ablation surface of the tip to remove the plaque and deposits to which it comes into contact. The atherectomy device of the present invention has application in a variety of vessels such as the coronary arteries, peripheral vessels such as the tibial artery, femoral, and popliteal, and saphenous vein bypass grafts.

In order for the atherectomy tip to reach the vessel stenosis (obstruction) it is supported on a flexible shaft and inserted along with the flexible shaft through an introducer sheath and over a guidewire. More specifically, the introducer sheath is placed through a skin incision and into a vessel, e.g., the femoral artery in the patient's leg, to provide access to the target site. A guidewire is then inserted through the introducer sheath and advanced through the appropriate vessels to the target obstructed site, typically the coronary artery. The flexible shaft and attached atherectomy tip are then inserted through the introducer sheath and threaded over the length of the guidewire to the target obstructed site. Actuation of the motor spins the shaft and tip so the cutting surface repeatedly comes into contact with the obstruction, e.g., plaque, to remove it from the vessel wall.

Details of the present invention will now be described with reference to the drawings wherein like reference numerals identify similar or like components throughout the several views.

Figure 13:
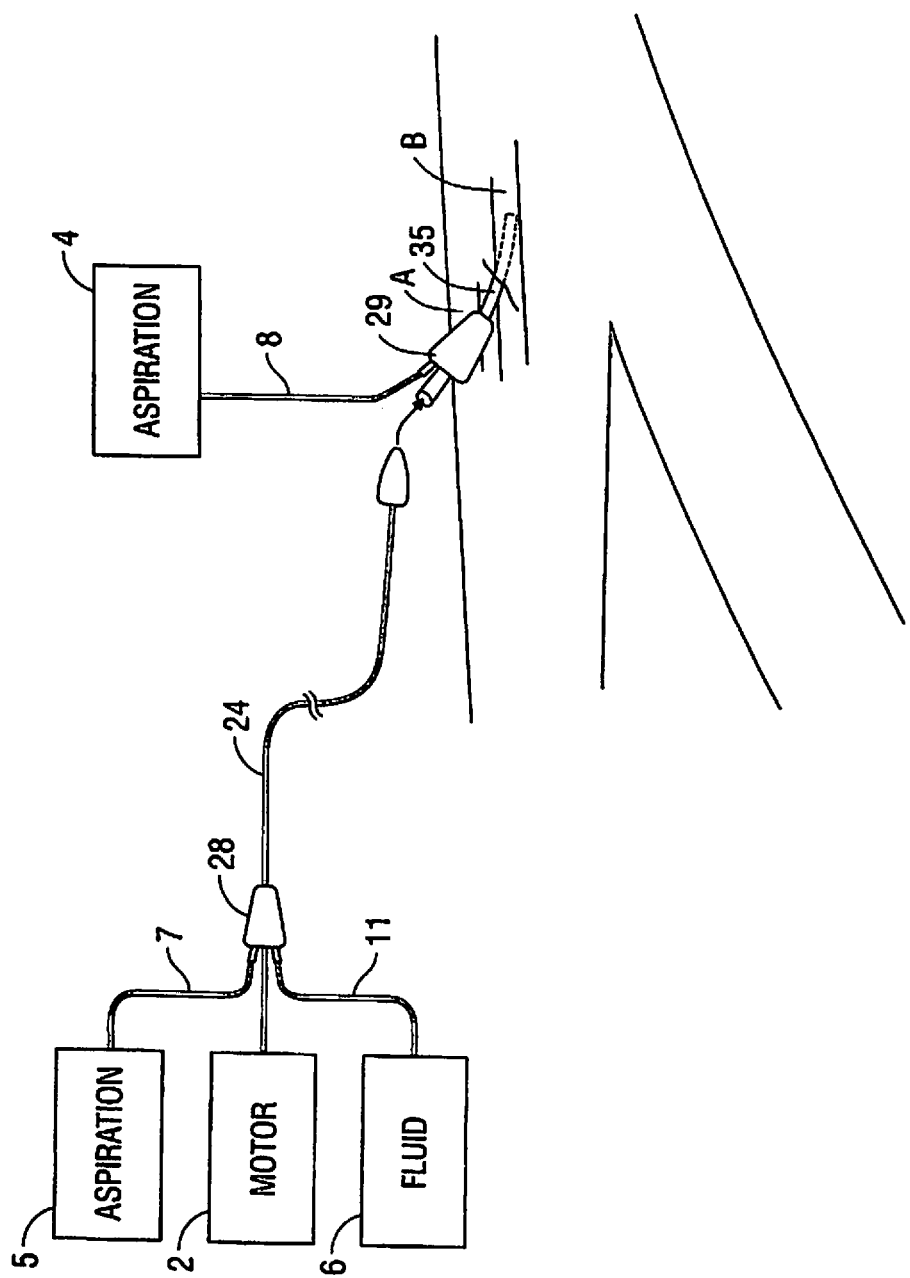
FIG. 13 is a schematic view illustrating the atherectomy system of one embodiment of the present invention.

FIG. 1 illustrates one embodiment of the atherectomy device of the present invention, designated generally by reference numeral 10. The entire device is shown in FIG. 13; the distal portion of the device is shown in FIGS. 1-3. The atherectomy tip or bit 12 of the device 10 is connected to a flexible inner shaft 20 such that rotation of the inner shaft 20 rotates the tip 12. As shown, the tip 12 is connected at a distal region of the rotatable shaft 20, but preferably spaced from a distalmost end 22 of inner shaft 20. The flexible shaft 20 is electrically powered for high speed rotation to rotate the shaft 20 and tip 12 to break up plaque to treat stenosis of a vessel. A motor housing 2, shown schematically in FIG. 13, contains a motor mounted therein and a motor shaft (not shown). The atherectomy device 10 is operatively connected to the motor housing 2 such that activation of the motor rotates the shaft 20 of the device. A control knob can be provided to adjust the rotational speed of the shaft 20 and tip 12, and a window can be provided to visually display the speed. Shaft 20 and tip 12 can be disposable. In use, an introducer sheath or catheter is inserted through an incision "A" in the patient's leg, and through an incision in the femoral artery "B". The catheter 24 with attached shaft 20 (positioned therein) and tip 30 are thus introduced through the introducer sheath 35 into the femoral artery "B", and advanced to the target artery, e.g., the coronary artery, to the treatment obstruction site. Note that a guidewire G extends through the shaft 20 and into the target artery so that the shaft 20 and tip 12 are inserted over the guidewire. FIG. 13 illustrates an exemplary introducer sheath 35.

The system in some embodiments further includes a vacuum source 5, shown schematically in FIG. 13, communicating with the catheter 24 to aspirate particles from the catheter 24 in the space (lumen 27) between the catheter 24 and shaft 20. Tubing 7 extends from the aspiration source 5 to the catheter 24, through catheter hub 28, and in some embodiments through a side arm (not shown) in catheter hub 28. The system in some embodiments can have an aspiration source 4 communicating with the introducer sheath 35 via hub 29, and in some embodiments through a side port in hub 29, to provide aspiration in the space between the sheath 35 and the outer wall of catheter 24. Note the aspiration through the introducer sheath 35, if provided, can be in addition to the aspiration through catheter 24 or alternatively the sole source of aspiration. The system can also include a fluid source for delivering fluids to the vessel. Tubing 11 extends from the fluid source 6, through catheter hub 28, and in some embodiments through a side arm in catheter hub 28, to communicate with the inner lumen of the shaft.

It should be appreciated that the device 10 is shown inserted through the femoral artery by way of example as other vessels can be utilized for access, such as the radial artery. Also, the tip of the present invention can be used to remove plaque or other obstructions in a variety of vessels such as the coronary artery, the tibial artery, the superficial femoral, popliteal, saphenous vein bypass grafts and instent restenosis.

With reference to FIGS. 1-3, the first embodiment of the atherectomy tip of the present invention will now be described in more detail. Tip or burr 12 has a front (distal) portion (section) 14, a rear (proximal) portion (section) 16, and an intermediate portion (section) 18 between the front and rear portions 14 and 16. These portions vary in transverse cross-section as can be appreciated by the Figures. Thus, the front portion 14 can be defined for convenience as the area starting at the distalmost tip 17, forming a bullet nose configuration. The cross-section of the front portion 14 in one embodiment is substantially circular in configuration. The intermediate portion 18 can be considered as the region where the tip 12 transitions into the scalloped region 19. The cross-section of the intermediate portion 18 progressively changes from substantially circular, to an elongated shape having two substantially flat or linear opposing sidewalls 16a. This can also be viewed as removed material from the otherwise conical shape so that the distance between opposing linear walls 16a is less than the distance between opposing walls 19a.

Rear portion 16 can be considered to begin, for convenience, in the scalloped region 19, and terminate at the proximalmost edge 13 of tip 12. The rear portion 16 preferably has the same elongated cross-sectional dimension throughout its length, with substantially linear walls 16a separated by a distance less than the distance between opposing walls 19a.

The scalloped or narrowed section 19 is formed in both sides of the tip 12 to reduce the profile of the tip 12. These scalloped sections form the aforedescribed opposing substantially linear walls. By reducing the profile, i.e., the diameter and circumference, the atherectomy tip of the present invention could be inserted through smaller introducer sheaths than would otherwise be the case if the circumference increased with increasing diameter.

It should also be appreciated that the front, intermediate and rear portions/sections are designated for convenience and are not intended to require three separate segments connected together. Tip 12 can be, and is preferably, a monolithic piece.

Tip 12 has a proximal or rear opening 32 and a distal or front opening 34 connected by a lumen. The flexible shaft 20 extends through openings 32, 34 and the lumen and is attached to the tip 12. In some embodiments, the tip 12 is attached such that the shaft 20 extends through front opening 34 and extends a short distance distal of distalmost edge 17 of tip 12. Shaft 20 has lumen 25 dimensioned to receive a guidewire G to enable over the wire insertion of the atherectomy device 10.

The region of plaque removal is defined by the largest diameter region of the tip since the tip is rotating at high speeds and the plaque is cut or abraded only where the tip comes into contact with it. However, the sheath size required is determined by the largest circumference region of the tip. In certain embodiments, the region of plaque removal can be further increased by altering the geometry and/or material of the tip 12 to create a wobbling effect which is described in more detail below.

As a result of the scalloped sections of the tip, as the diameter of tip 12 increases in one orientation, it decreases in the transverse orientation, enabling the circumference to remain constant. Since the diameter is reduced in one transverse orientation, the tip 12 can be introduced into an introducer sheath have an internal diameter slightly less than the largest diameter of the tip, since the sheath has room to deform because of the reduced regions, i.e., the scalloped sections, of the tip 12. In the prior art elliptical tip, the rounded symmetrical configuration leaves no room for the sheath to deform so the sheath size must exceed the largest diameter region. Thus, the tip 12 of the present invention can fit into conventional introducer sheaths having an internal diameter less than the largest outer diameter of the tip 12. This can be achieved by the fact that the tip 12 can deform the internal walls of the sheath as it is inserted, by ovalizing the sheath. If the scalloped walls were not provided, the sheath would need to stretch, rather than ovalize to allow an oversized tip to pass.

Another way to view the tip 12 is that for a given catheter French size desired to be used by the surgeon, a larger atherectomy tip can be utilized if the atherectomy tip 30 of the present invention is selected instead of the prior art elliptical tip, thereby advantageously increasing the region of plaque removal to create a larger passageway in the vessel.

In alternate embodiments of the tip 12, longitudinal or elongated circular and oval cutting grooves could be provided to provide a roughened surface to cut or ablate the plaque as the tip is rotated. The grooves or indentations can be formed by laser cutting a series of grooves extending longitudinally within the interior of the tip stock. The tip is then ground to remove portions of the outer surface to partially communicate with the grooves, thereby creating indentations forming a roughened surface for contact with the plaque. The resulting formation is a series of elongated cutouts/indentations on the front and intermediate portions and oval shaped cutouts/indentations on the distal and intermediate portions.

Another way contemplated to create the roughened surface is by blasting, e.g. sandblasting or grit blasting, the tip. The tip is held in a fixture and blasted at a certain pressure, thereby removing portions of the outer surface to create a roughened surface. Creation of a roughened surface by chemical etching is also contemplated. In an alternate embodiment, an abrasive coating, such as diamond particles, is applied to the tip.

Figure 9:
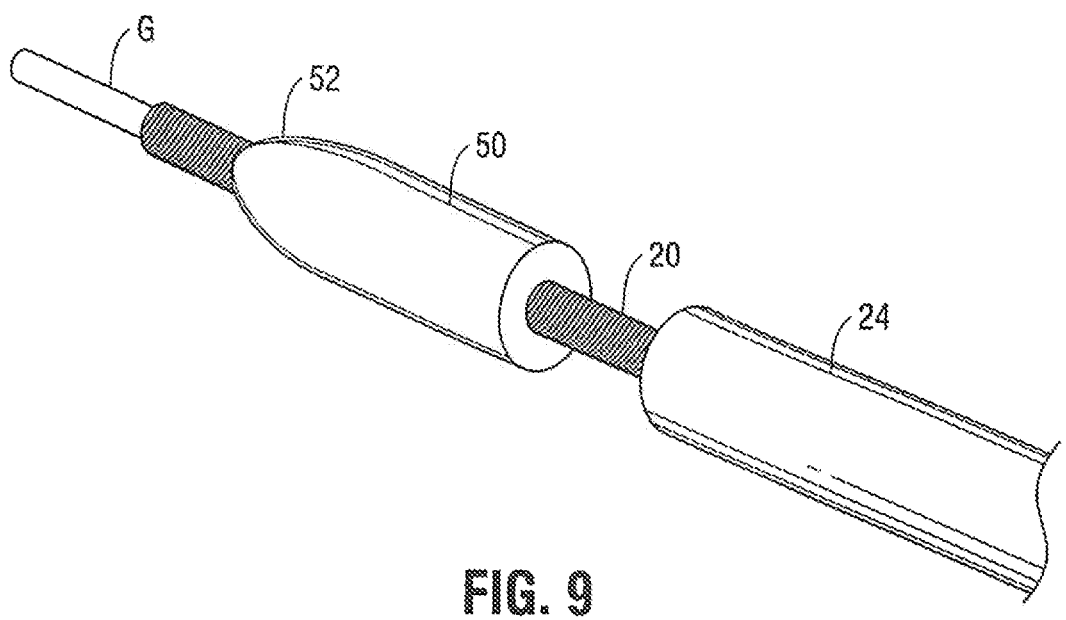
FIG. 9 is a perspective view of a distal portion of another alternate embodiment of the atherectomy device of the present invention.

FIG. 9 illustrates an alternate embodiment of the atherectomy tip. In this embodiment, the tip, designated generally by reference numeral 50, does not have scalloped sections but instead is substantially cylindrical in configuration along its length except for the bullet nose tip. That is, it is circular in transverse cross-section throughout its length. In all other respects, the atherectomy device of FIG. 9 is the same as FIG. 1, i.e., includes shaft 20 extending beyond the atherectomy tip, catheter 24, etc., so for brevity these components will not be discussed herein since the discussion of these components with respect to FIG. 1 are fully applicable to the embodiment of FIG. 9.

Figure 3A:
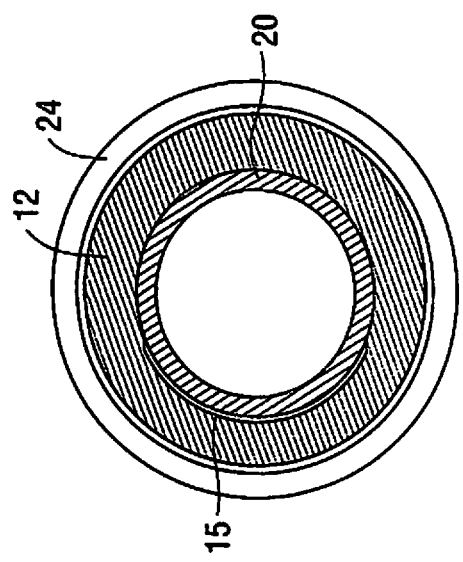
FIG. 3A is a transverse cross-sectional view of the tip of FIG. 1.

In some embodiments, the tip 12 or tip 50 is symmetrical. In alternate embodiments, the outer geometry of the tip is symmetrical, however, an inner portion of one side of the tip is carved out or removed to create an imbalance resulting in an offset center of mass. This results in wobbling of the tip during high speed rotation which in turn enables a spinning diameter to exceed the cross-sectional dimension of the tip. In this manner, the tip can be used to remove plaque in a wider transverse area. This is shown in FIG. 3A with material removed from one side of the tip 12 to create a cutout or removed material section 15.

Removing material from one side of the tip is one way to achieve this wobbling effect. Another way is through the tip itself being composed of materials of different density, either the same material of different densities or different materials of a differing density such as in FIG. 10B. Such materials utilized can include by way of example platinum and aluminum. These two ways of achieving the wobbling effect are also disclosed below in conjunction with the two piece tip.

As shown, the tip 12 is fixed to the shaft 20 and positioned distal of the end of the catheter 24. The shaft 20 is axially fixed within catheter 24 but can rotate with respect to the catheter 24. The tip 12 therefore remains distal of the opening 23 in the catheter 24 to maintain the gap e.g., a fixed gap, between the proximal edge 13 of the tip 12 and the opening 23 so particles can be aspirated through the opening 23 and lumen 27 of the catheter 24.

Figure 11A:
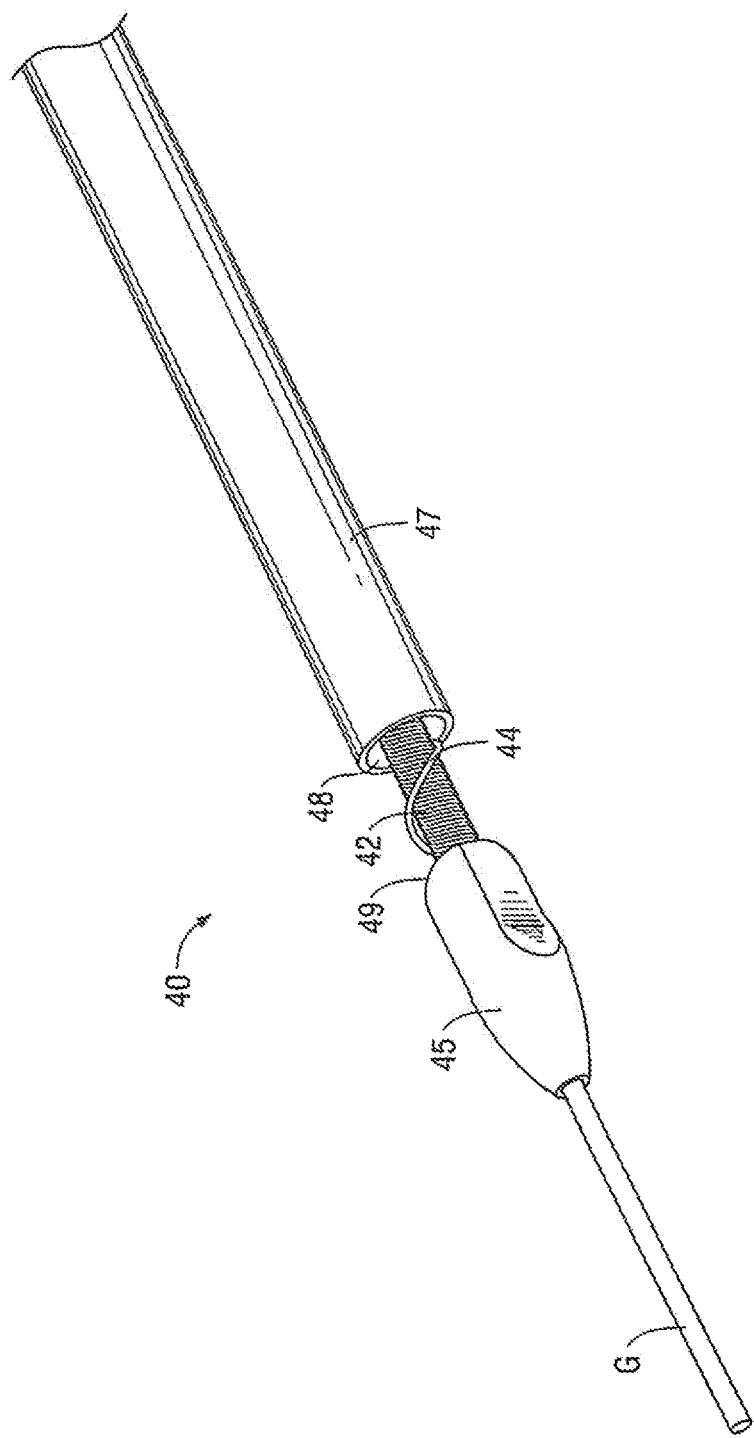
FIG. 11A is perspective view of a distal portion of another alternate embodiment of the atherectomy device of the present invention.
Figure 11B:
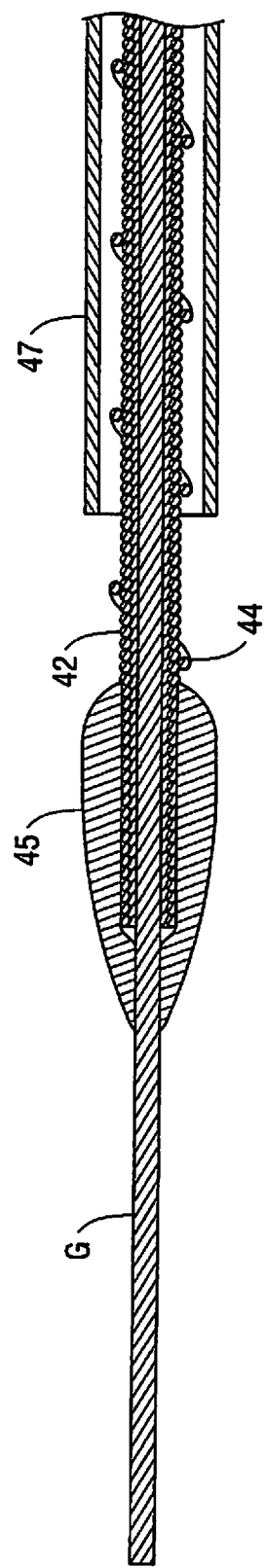
FIG. 11B is a longitudinal cross-sectional view of the device of FIG. 11A.

In the alternate embodiment of FIGS. 11A and 11B, device 40 includes a shaft 42 having an auger or series of threads 44 proximal of tip or bit 45. The auger 44 is positioned on the region of the shaft 42 proximal of the proximal edge 49 of tip 45 and extends along a length of the shaft 42 within outer tube or catheter 47. These threads 44 function as an Archimedes screw, i.e., a screw pump, to remove the plaque. That is, as the shaft 42 is rotated in the same manner as shaft 20, the screw's helical surface scoops particles and directs the particles proximally (rearwardly) along the shaft 20 through the lumen of catheter 47. In all other respects, device 40 is identical to device 10. The auger 44 can be used in addition to an aspiration source for aspirating particles into the opening 48 of catheter 47 (as in the embodiment of FIGS. 1-3) or alternatively used as a substitute so it provides the sole mechanism for aspirating particles through the lumen of the catheter 47. The auger 44 can extend along the entire length or along a partial length of the shaft 20. The auger 44 for removing particles can be used with any of the atherectomy devices disclosed herein.

FIGS. 4-8, 10A and 10B illustrate alternate embodiments of the atherectomy tip of the present invention wherein the tip is composed of two separated components. More particularly, in the embodiment of FIGS. 4-8 and 10A, the tip 60 of atherectomy device 61 has a first component 62 and a second component 64. Tip 60 is mounted on shaft 70 (similar to shaft 20) at a position spaced proximally from the distalmost edge 72 of the shaft 70 so that a distal portion of the shaft 70 extends slightly distally of the distalmost edge 65 of tip 60. Shaft 70 is rotatably mounted within lumen 82 of catheter 80 but axially fixed within catheter 80 to create a fixed gap between the tip 60 and catheter 80. The shaft 70 has a lumen for insertion over a guidewire G.

With reference to FIGS. 5-8 and 10A, tip component 62 has a cutout or removed material portion 66 to reduce the amount of material of the tip. Tip component 64 does not have such cutout. In this manner, due to the material imbalance which creates an offset center of mass, the tip 60 will wobble when rotated to remove plaque in an area greater than a transverse dimension of the tip 60.

Figure 10A:
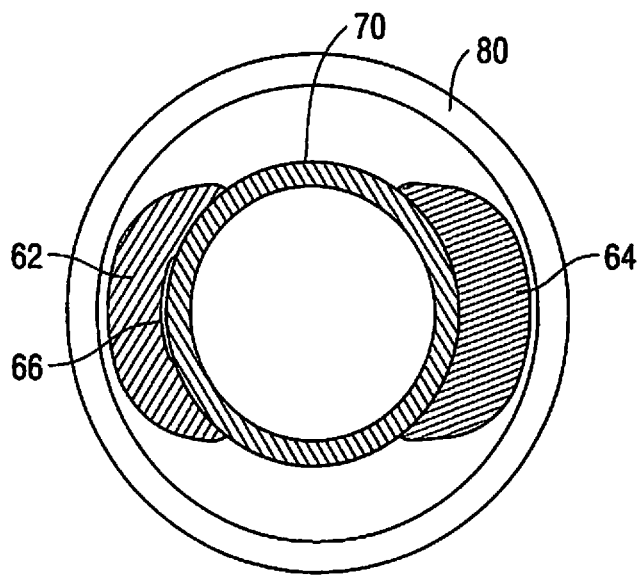
FIG. 10A is a transverse cross-sectional view of the bit of FIG. 4.
Figure 10B:
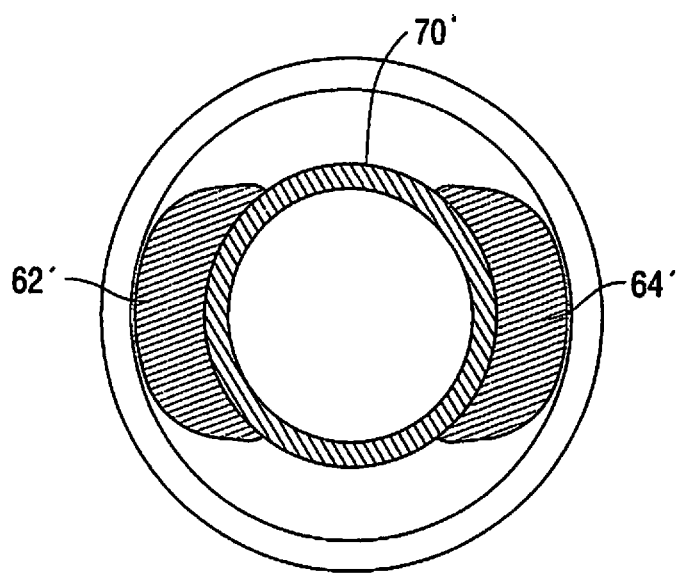
FIG. 10B is a view similar to FIG. 10A showing an alternate embodiment of the atherectomy bit of the present invention.

In the embodiment of FIG. 10B, the two tip components 62', 64' have different densities to achieve the wobbling effect.

Figure 4:
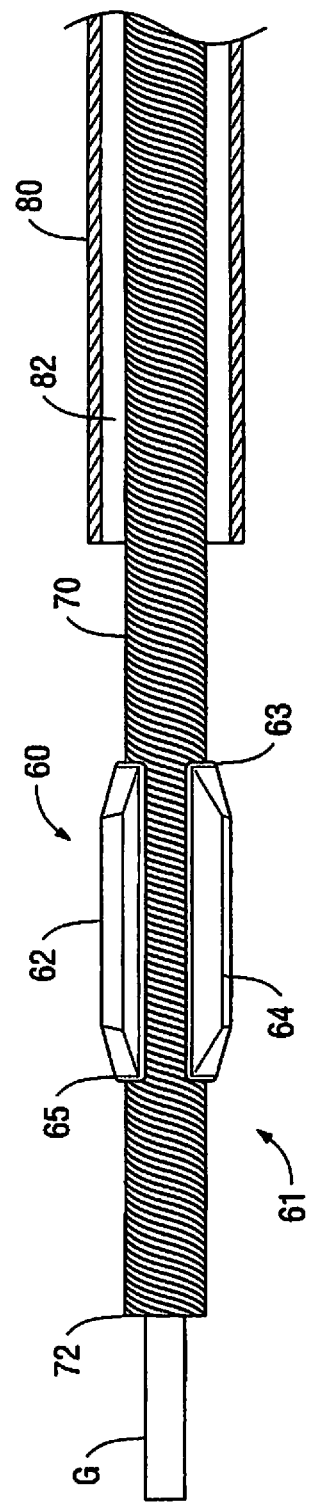
FIG. 4 is a partial cross-sectional view of the distal portion of an alternate embodiment of the atherectomy device of the present invention.
Figure 5:
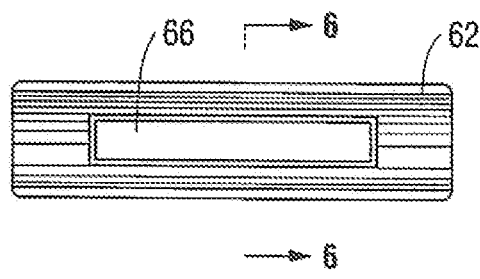
FIG. 5 is a cut away side view of the atherectomy bit of FIG. 4.
Figure 6:
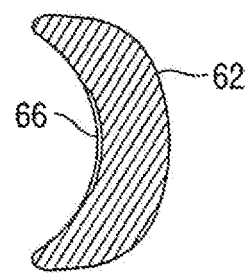
FIG. 6 is a transverse cross-sectional view taken along line 6-6 of FIG. 5.
Figure 7:
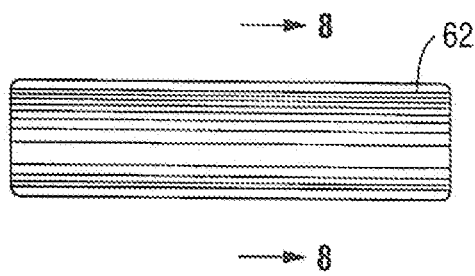
FIG. 7 is a cut away side view of the bit of FIG. 4 showing the opposite side of the side shown in FIG. 5.
Figure 8:
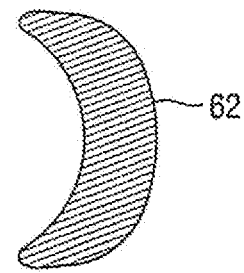
FIG. 8 is a transverse cross-sectional view taken along line 8-8 of FIG. 7.
Figure 12A:
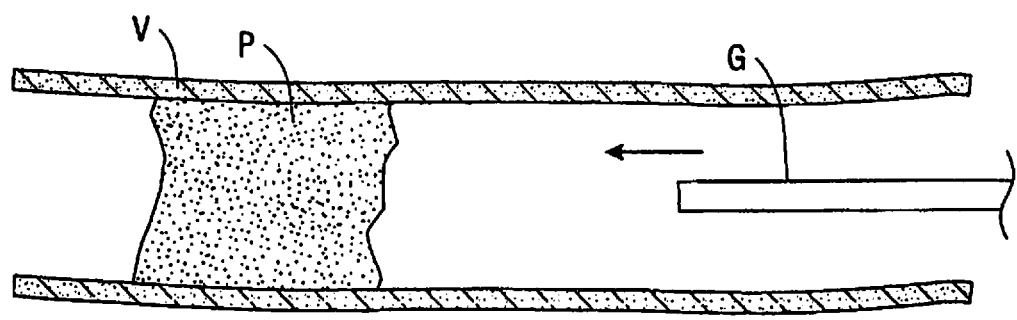
Figure 12B:
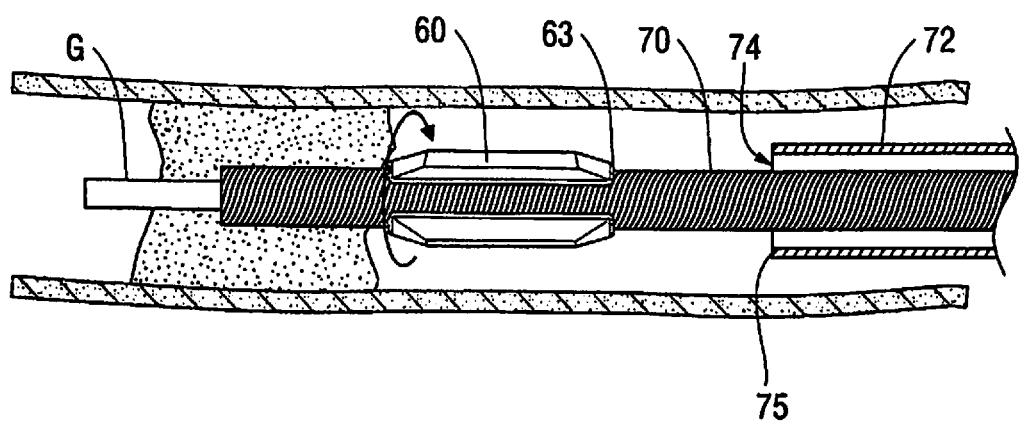
Figure 12C:
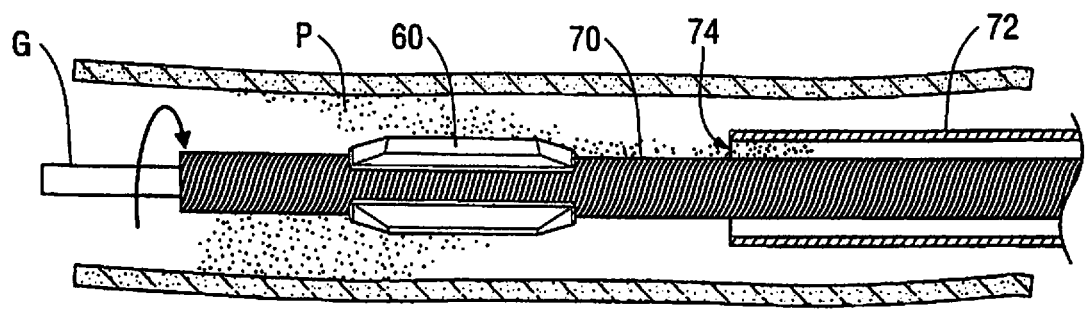
Figure 12D:
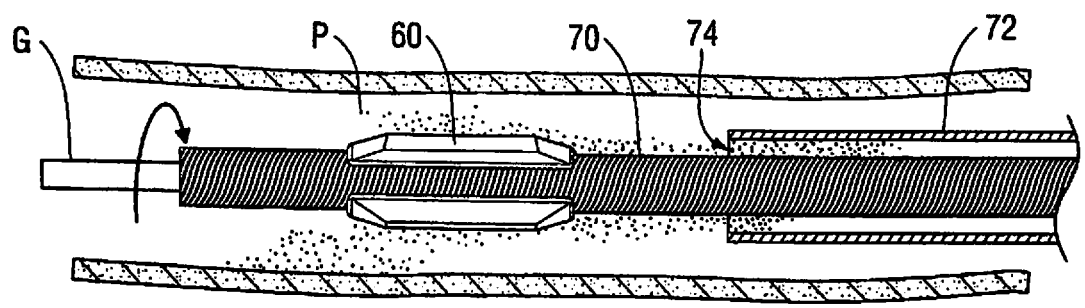

Use of the atherectomy tip of the present invention is illustrated in FIGS. 12A-12D. The tip 60 of FIG. 4 is shown in these drawings, it being understood that the other atherectomy devices and tips disclosed herein would be used in the same insertion and rotational manner. As shown in FIG. 12A, plaque "P" buildup on the interior wall of the vessel "V" has occluded the passageway through the vessel. Rotational shaft 70 with attached tip 60 (or tip 12 or any of the other tips disclosed herein) is inserted over guidewire G and by motorized rotation of flexible rotatable shaft 70 is rotated at high speed in the direction of the arrow in FIG. 12B to remove plaque which comes into contact with its outer surface. Aspiration is provided to aspirate the broken off particles through opening 74 in catheter 72. The gap between the distal edge 75 of catheter 72 and the proximalmost edge 63 of tip 62 provides space for the particles to be suctioned through opening 74. Thus, the cut plaque and debris can be removed from the patient's body as the particles are dislodged by the rotating tip 60 as shown in FIG. 12C. As the plaque is removed, the device is continually advanced to continue to remove the plaque as shown in FIG. 12D. As noted above, an auger like auger 44 can be provided in lieu of or in addition to an aspiration source.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. An atherectomy device for removing deposits such as plaque from an interior of a vessel comprising:
   an outer member having a distal end;
   a rotatable shaft positioned for rotational movement within the outer member and fixed axially within the outer member, the shaft having a longitudinal axis, a distal region and a distalmost edge; and
   a rotatable tip having a proximal end and a distal end, the proximal end of the rotatable tip positioned distally of the distalmost edge of the outer member to create a fixed gap between the proximal end of the rotatable tip and the distalmost edge of the outer member, the rotatable tip mounted to the distal region of the rotatable shaft and having a longitudinal axis and mounted to the rotatable shaft for rotation about its longitudinal axis upon rotation of the rotatable shaft, the rotatable shaft including a guidewire lumen for receiving a guidewire to enable over the wire insertion of the device;
   wherein the rotatable tip comprises a rotatable bit having a proximalmost end and a distalmost end and a distance between the proximalmost end and the distalmost end remains constant during delivery and use of the device to define a fixed length; and
   wherein a cutting surface of the rotatable bit contacts and removes the deposits from the vessel.

2. The atherectomy device of claim 1, further comprising an auger positioned on the rotatable shaft, the auger positioned proximally of the rotatable tip and extending along the rotatable shaft, wherein rotation of the rotatable shaft rotates the auger to move particles macerated by the rotatable tip proximally into the outer member.

3. The atherectomy device of claim 2, wherein particles are configured to be aspirated through the outer member in the space between the rotatable shaft and an inner wall of the outer member.

4. The atherectomy device of claim 1, wherein particles are configured to be aspirated through the outer member in the space between the rotatable shaft and an inner wall of the outer member.

5. The atherectomy device of claim 4, wherein the rotatable tip is spaced from a distalmost end of the rotatable shaft.

6. The atherectomy device of claim 1, wherein the rotatable tip is made of first and second materials, the first material having a first density and the second material having a second density less than the first density.

7. The atherectomy device of claim 6, wherein the material of the first density is on one side of the rotatable tip and the material of the second density is on the other side of the rotatable tip.

8. The atherectomy device of claim 1, wherein the rotatable tip has a first region on one side of a longitudinal axis of the shaft and a second region on an opposing side of the longitudinal axis of the rotatable shaft, and the first region has a cutout so a first amount of material in the first region is less than a second amount of material in the first region.

9. The surgical apparatus of claim 1, wherein the rotatable tip is positioned proximal of the distalmost edge of the rotatable shaft.

10. The atherectomy device of claim 1, wherein the rotatable tip has a first portion and a second portion, the first portion being different than the second portion.

11. The atherectomy device of claim 10, further comprising an auger positioned on the rotatable shaft, the auger positioned proximally of the rotatable tip and extending along the rotatable shaft, wherein rotation of the rotatable shaft rotates the auger to move particles macerated by the rotatable tip proximally into the outer member.

12. The atherectomy device of claim 1, wherein the rotatable bit has a lumen to receive the rotatable shaft.

13. The atherectomy device of claim 1, in combination with an introducer sheath, the outer member and rotatable shaft movable within the introducer sheath.

14. The atherectomy device of claim 1, wherein the rotatable tip remains distal of a distalmost edge of the outer member during insertion and use of the device.

15. An atherectomy device for removing deposits such as plaque from an interior of a vessel comprising:

an outer member having a distal end;

a rotatable shaft positioned for rotational movement within the outer member and fixed axially within the outer member, the shaft having a longitudinal axis, a distal region and a distalmost edge; and a rotatable tip having a proximal end and a distal end, the proximal end of the rotatable tip positioned distally of the distalmost edge of the outer member to create a fixed gap between the proximal end of the rotatable tip and the distalmost edge of the outer member, the rotatable tip mounted to the distal region of the rotatable shaft and having a longitudinal axis and mounted to the rotatable shaft for rotation about its longitudinal axis upon rotation of the rotatable shaft, the rotatable shaft including a guidewire lumen for receiving a guidewire to enable over the wire insertion of the device, wherein the rotatable tip is composed of first and second components, the first and second components radially spaced from each other, and the first component is composed of a material having a density greater than the second component.

16. The surgical apparatus of claim 15, wherein the first component has a portion removed so it is composed of less material than the second component.

* * * * *